(12) United States Patent
Moffitt

(10) Patent No.: US 10,994,142 B2
(45) Date of Patent: May 4, 2021

(54) DETERMINATION AND USE OF A WELLNESS FACTOR IN AN IMPLANTABLE MEDICAL DEVICE SYSTEM USING QUALITATIVE AND QUANTITATIVE MEASUREMENTS

(71) Applicant: Boston Scientific Neuromodulation Corporation, Valencia, CA (US)

(72) Inventor: Michael A. Moffitt, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 121 days.

(21) Appl. No.: 16/393,583

(22) Filed: Apr. 24, 2019

(65) Prior Publication Data

US 2019/0344081 A1  Nov. 14, 2019

Related U.S. Application Data

(60) Provisional application No. 62/669,207, filed on May 9, 2018.

(51) Int. Cl.
  *A61N 1/36* (2006.01)
  *A61N 1/05* (2006.01)

(52) U.S. Cl.
  CPC .......... *A61N 1/36139* (2013.01); *A61N 1/05* (2013.01); *A61N 1/36071* (2013.01); *A61N 1/36125* (2013.01)

(58) Field of Classification Search
  CPC .. A61N 1/05; A61N 1/36071; A61N 1/36125; A61N 1/36132; A61N 1/36139
  See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 7,647,116 B2 | 1/2010 | Bauhahn | |
| 7,647,117 B2 | 1/2010 | Bauhahn | |
| 7,853,322 B2 | 12/2010 | Bourget et al. | |
| 7,957,797 B2 | 6/2011 | Bourget et al. | |

(Continued)

OTHER PUBLICATIONS

U.S. Appl. No. 62/648,231, Esteller et al., filed Mar. 26, 2018.

(Continued)

*Primary Examiner* — George Manuel
(74) *Attorney, Agent, or Firm* — Lewis & Reese, PLLC

(57) ABSTRACT

A system is disclosed in one example which allows for modelling the wellness of a given Implantable Pulse Generator (IPG) patient. The modelling, embodied in an algorithm, uses one or more qualitative measurements and one or more quantitative measurements taken from the patient. The algorithm correlates the qualitative measurements to the various quantitative measurements to eventually, over time, learn which quantitative measurements best correlate to the qualitative measurements provided by the patient. The algorithm can then using current quantitative measurements predict a wellness factor or score for the patient, which is preferably weighted to favor the quantitative measurements that best correlate to that patient's qualitative assessment of therapy effectiveness. Additionally, the wellness factor may be used to adjust the stimulation program that the IPG device provides to the patient.

20 Claims, 7 Drawing Sheets

(56) References Cited

U.S. PATENT DOCUMENTS

| | | |
|---|---|---|
| 7,957,809 B2 | 6/2011 | Bourget et al. |
| 8,606,362 B2 | 12/2013 | He et al. |
| 8,620,436 B2 | 12/2013 | Parramon et al. |
| 8,788,055 B2 | 7/2014 | Gerber et al. |
| 9,259,574 B2 | 2/2016 | Aghassian et al. |
| 9,289,603 B1 | 3/2016 | Giuffrida et al. |
| 9,446,243 B2 | 9/2016 | Marnfeldt et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2014/0228905 A1* | 8/2014 | Bolea ............... A61F 5/56 607/42 |
| 2015/0231402 A1 | 8/2015 | Aghassian |
| 2015/0306391 A1 | 10/2015 | Wu et al. |
| 2015/0360038 A1 | 12/2015 | Zottola et al. |
| 2016/0082262 A1 | 3/2016 | Parramon et al. |
| 2016/0184591 A1 | 6/2016 | Feldman et al. |
| 2017/0056642 A1 | 3/2017 | Moffitt et al. |
| 2017/0151438 A1 | 6/2017 | Orinski |
| 2017/0182322 A1 | 6/2017 | Grill et al. |
| 2018/0071520 A1 | 3/2018 | Weerakoon et al. |
| 2018/0085055 A1 | 3/2018 | Annoni et al. |
| 2018/0085584 A1 | 3/2018 | Thakur et al. |
| 2018/0140831 A1 | 5/2018 | Feldman et al. |
| 2019/0083796 A1 | 3/2019 | Weerakoon et al. |
| 2019/0099602 A1 | 4/2019 | Esteller et al. |

OTHER PUBLICATIONS

The PainQX System, https://www.painqx.com/the-painqx-system (date unknown).
Medasense: Pain Monitoring Device: PMD-200, https://www.medasense.com/pain-monitoring-device-pmd-200-medasense-biometrics-ltd/ (2018).
Bliss Master: Features, https://sites.google.com/site/blissmaestro/home/features (date unknown).
Pain Assessment Tools, http://www.paincommunitycentre.org/article/pain-assessment-tools (date unknown).
Patients' Global Impression of Change (PGIC) Scale, http://www.chiro.org/LINKS/OUTCOME/Patients_Global_Impression_of_Change.pdf, (date unknown).
EQ-5D, https://en.wikipedia.org/wiki/EQ-5D (date unknown).
Mobi Health News: California Hospital Becomes First in US to Prescribe Ingestible Sensors from Proteus, http://www.mobihealthnews.com/content/california-hospital-becomes-first-us-prescribe-ingestible-sensors-proteus (Jan. 11, 2016).
International Search Report and Written Opinion regarding corresponding PCT Application No. PCT/US2019/028949, dated Aug. 5, 2019.

* cited by examiner

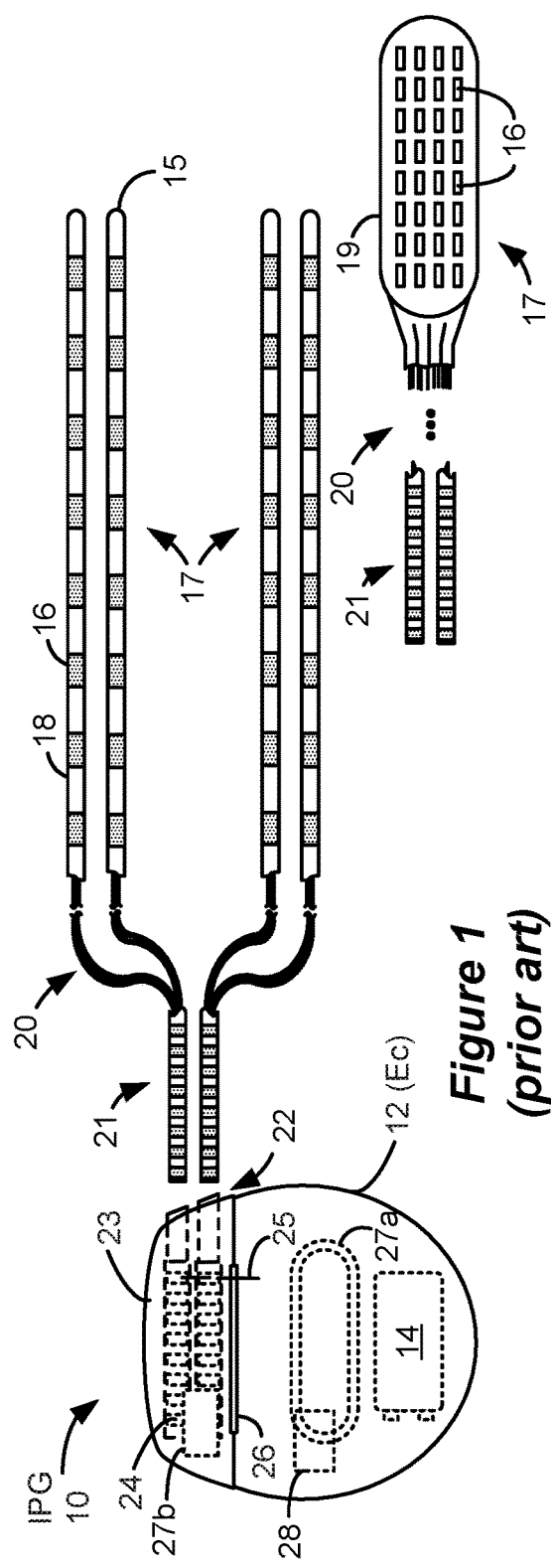
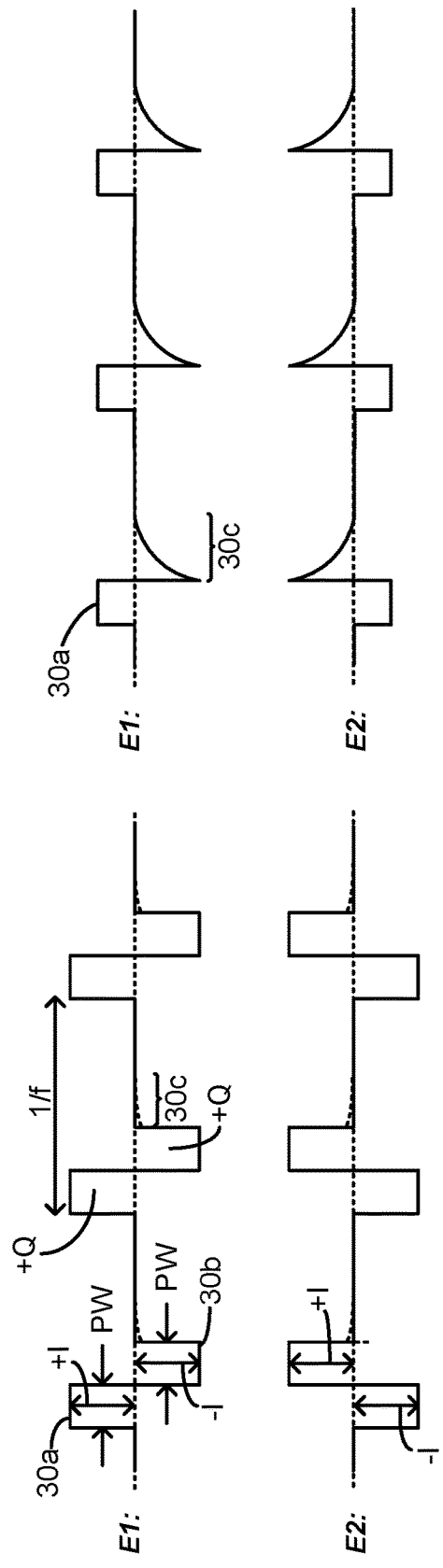
Figure 1 (prior art)
Figure 2 (prior art)

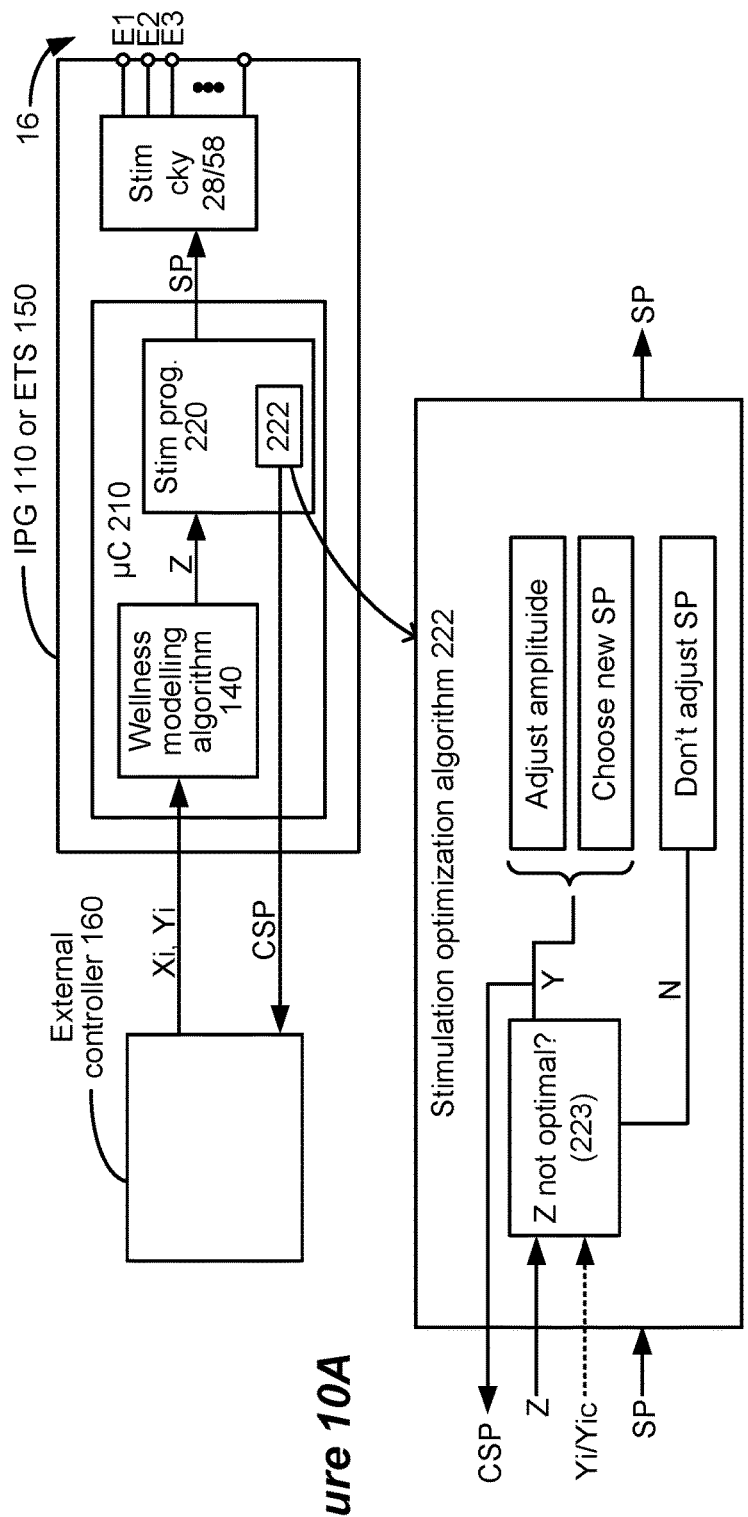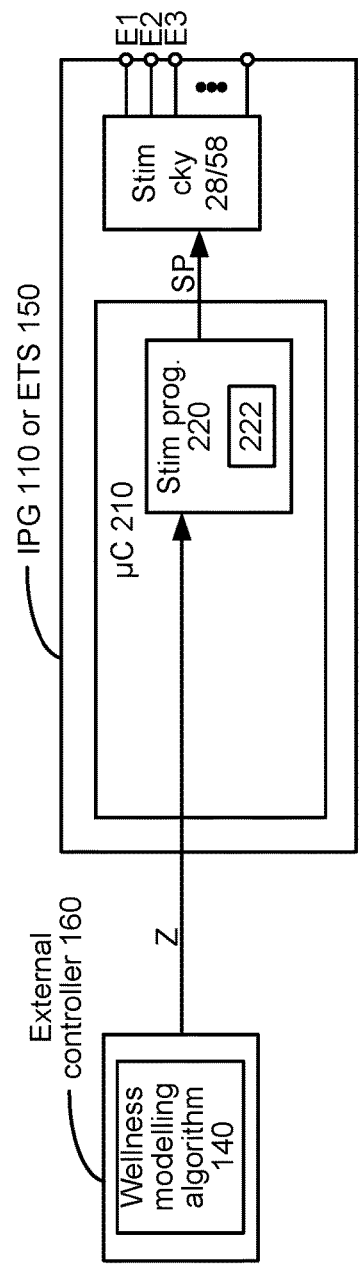
*Figure 10A*
*Figure 10B*

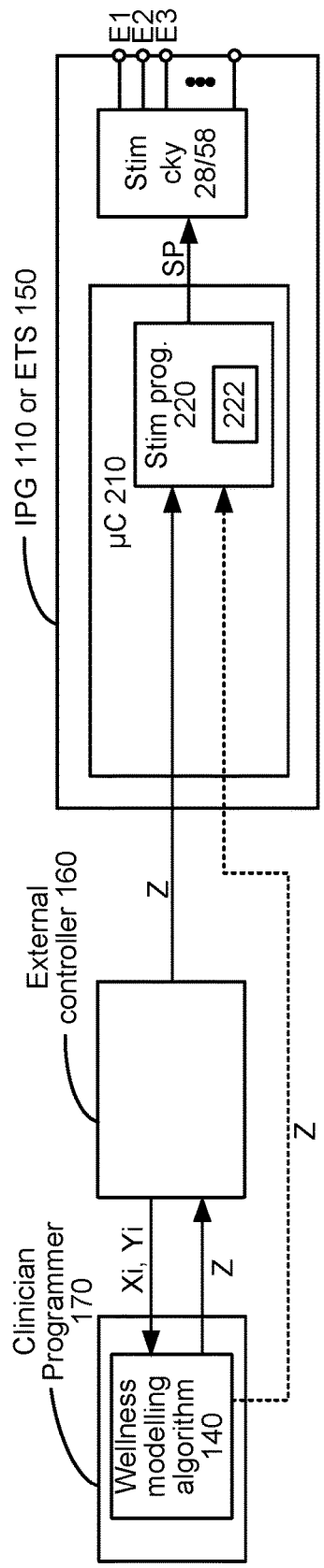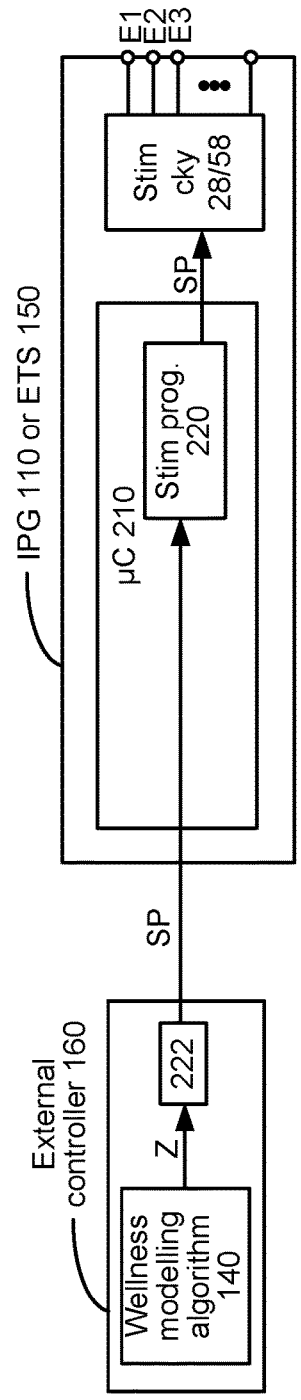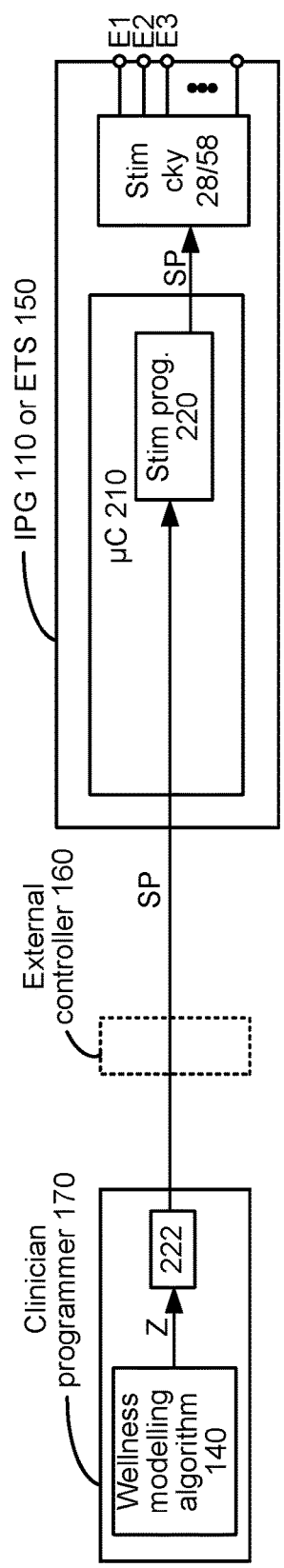
*Figure 10C*
*Figure 10D*
*Figure 10E*

DETERMINATION AND USE OF A WELLNESS FACTOR IN AN IMPLANTABLE MEDICAL DEVICE SYSTEM USING QUALITATIVE AND QUANTITATIVE MEASUREMENTS

CROSS REFERENCE TO RELATED APPLICATIONS

This is a non-provisional application of U.S. Provisional Patent Application Ser. No. 62/669,207, filed May 9, 2018, which is incorporated by reference, and to which priority to claimed.

FIELD OF THE INVENTION

This application relates to Implantable Medical Devices (IMDs), and more specifically to circuitry and method to create high- and low-frequency multiplexed pulses in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system or a Deep Brain Stimulation (DBS) system, such as disclosed in U.S. Pat. No. 6,516,227 and U.S. Patent Application Publication 2016/0184591. However, the present invention may find applicability in any medical device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, as is useful to alleviate chronic back pain for example, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22.

In a DBS application, as is useful in the treatment of tremor in Parkinson's disease for example, the IPG 10 is typically implanted under the patient's clavicle (collarbone), although head-mounted IPGs can also be used. See, e.g., U.S. Patent Application Publication 2017/0151438. When implanted under the clavicle, percutaneous leads 15 are tunneled through the neck and the scalp and the electrodes 16 are implanted through holes drilled in the skull and positioned for example in the Subthalamic Nucleus (STN) and the Pedunculopontine Nucleus (PPN) in each brain hemisphere. DBS can also be used for the treatment of neuropsychiatric disorders, such as depression, anxiety, fear, and other neuropsychiatric-related symptoms. For these indications, the electrodes 16 may be implanted in different areas of the brain, such Brodmann Area 25, the Subgenual Cingulate, the Medial Forebrain Bundle, the Ventral Capsule or Ventral Striatum, the Nucleus Accumbens, etc. Stimulation may occur in DBS using ring electrodes 16, but split-ring electrodes having directional capabilities can be useful, especially when coupled with multiple current source steering capability.

In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, WiFi, MICS, and the like.

Stimulation in IPG 10 is typically provided by pulses each of which may include a number of phases such as 30a and 30b, as shown in the example of FIG. 2. Stimulation parameters typically include amplitude (current I, although a voltage amplitude V can also be used); frequency (f); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program (SP) that the stimulation circuitry 28 in the IPG 10 can execute to provide therapeutic stimulation to a patient. Various examples of stimulation circuitries can be found in U.S. Pat. Nos. 6,181,969, 8,606,362, 8,620,436, and U.S. Patent Application Publications 2018/0071520 and 2019/0083796.

In the example of FIG. 2, electrode E1 has been selected as an anode (during its first phase 30a), and thus provides pulses which source a positive current of amplitude +I to the tissue. Electrode E2 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). Monopolar stimulation, in which the conductive case acts as an electrode, can also be used. More than one electrode may be selected to act as an anode at a given time, and more than one electrode may be selected to act as a cathode at a given time. Note that at any time the current sourced to the tissue (e.g., +I at E1 during phase 30a) equals the current sunk from the tissue (e.g., −I at E2 during phase 30a) to ensure that the net current injected into the tissue at any time is zero. The stimulation pulses as shown to the left in FIG. 2 are biphasic, with each pulse comprising a first phase 30a followed thereafter by a second phase 30b of opposite polarity. As is known, biphasic pulses are useful to actively recover any charge that might be stored on capacitive elements in the electrode current paths, such as on the DC-blocking capacitors (not shown) that intervene between the stimulation circuitry's outputs and the electrodes 16. The second pulses phases 30 may be followed by passive charge recovery periods 30c, during which the electrode nodes are shorted to a common reference voltage to equilibrate any remaining charge on capacitive elements, as explained for example in U.S. Patent Application Publication 2018/0140831. Alternatively, and as shown to the right in FIG. 2, the pulses may be monophasic, consisting of a single actively-driven pulse phase 30a, followed by a passive charge recovery 30c phase.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial electrode arrays 17' (e.g., one or more trial percutaneous leads 15 or trial paddle leads 19) are implanted in the patient's tissue at a target location 52, such as within the spinal column as explained earlier. The proximal ends of the trial electrode array(s) 17' exit an incision 54 in the patient's tissue and are connected to an External Trial Stimulator (ETS) 50. The ETS 50 generally mimics operation of the IPG 10, and thus can provide stimulation to the patient's tissue as explained above. See, e.g., U.S. Pat. No. 9,259,574, disclosing a design for an ETS. The ETS 50 is generally worn externally by the patient for a short while (e.g., two weeks), which allows the patient and his clinician to experiment with different stimulation parameters to hopefully find a stimulation program that alleviates the patient's symptoms (e.g., pain, tremor, depression, etc.). If external trial stimulation proves successful, the trial electrode array(s) 17' are explanted, and a full IPG 10 and a permanent electrode array 17 (e.g., one or more percutaneous 15 or paddle 19 leads) are implanted as described above; if unsuccessful, the trial electrode array(s) 17' are simply explanted.

Like the IPG 10, the ETS 50 can include one or more antennas to enable bi-directional communications with external devices such as those shown in FIG. 4. Such antennas can include a near-field magnetic-induction coil antenna 56a, and/or a far-field RF antenna 56b, as described earlier. ETS 50 may also include stimulation circuitry 58 (FIG. 4) able to form stimulation in accordance with a stimulation program, which circuitry may be similar to or comprise the same stimulation circuitry 28 (FIG. 3) present in the IPG 10. ETS 50 may also include a battery (not shown) for operational power.

FIG. 4 shows various external devices that can wirelessly communicate data with the IPG 10 or ETS 50, including a patient, hand-held external controller 60, and a clinician programmer 70. Both of devices 60 and 70 can be used to wirelessly transmit a stimulation program to the IPG 10 or ETS 50—that is, to program their stimulation circuitries 28 and 58 to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10 or ETS 50, such as various status information, etc.

External controller 60 can be as described in U.S. Patent Application Publication 2015/0080982 for example, and may comprise a controller dedicated to work with the IPG 10 or ETS 50. External controller 60 may also comprise a general purpose mobile electronics device such as a mobile phone which has been programmed with a Medical Device Application (MDA) allowing it to work as a wireless controller for the IPG 10 or ETS, as described in U.S. Patent Application Publication 2015/0231402. External controller 60 includes a user interface, preferably including means for entering commands (e.g., buttons 65 or selectable graphical icons) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64a capable of wirelessly communicating with the coil antenna 27a or 56a in the IPG 10 or ETS 50. The external controller 60 can also have a far-field RF antenna 64b capable of wirelessly communicating with the RF antenna 27b or 56b in the IPG 10.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 includes a coil antenna 27a, wand 76 can likewise include a coil antenna 80a to establish near-filed magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27b or 56b, the wand 76, the computing device 72, or both, can likewise include an RF antenna 80*b* to establish communication at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at https://www.intel.com/content/www/us/en/products/processors/core/i5-processors.html. Such control circuitry 88, in addition to executing the clinician programmer software 84 and rendering the GUI 82, can also enable communications via antennas 80*a* or 80*b* to communicate stimulation parameters chosen through the GUI 82 to the patient's IPG 10.

The user interface of the external controller 60 may provide similar functionality because the external controller 60 can include the same hardware and software programming as the clinician programmer. For example, the external controller 60 includes control circuitry 66 similar to the control circuitry 88 in the clinician programmer 70, and may similarly be programmed with external controller software stored in device memory.

SUMMARY

A medical device system is disclosed, which may in a first example comprise: a medical device configured to execute a program to alleviate a symptom of a patient; and at least one non-transitory computer readable medium containing instructions for a first algorithm, wherein the first algorithm when executed is configured to: receive at least one qualitative measurement from the patient regarding the symptom, receive a plurality of quantitative measurements taken from the patient, and determine a wellness factor for the patient using the at least one qualitative measurement and the plurality of quantitative measurements.

A medical device system is disclosed which may in a second example comprise: a medical device configured to execute a program to provide therapy to a patient; and at least one non-transitory computer readable medium containing instructions for a first algorithm, wherein the first algorithm when executed is configured to: receive at least one qualitative measurement from the patient regarding a status of the patient, receive a plurality of quantitative measurements taken from the patient, and determine a wellness factor for the patient using the at least one qualitative measurement and the plurality of quantitative measurements, wherein the wellness factor is indicative of the status of the patient.

In either of the first or second examples, the first algorithm may be configured to be executed on an external device configured to adjust the program executed by the medical device. The first algorithm may further be configured to receive at least one of the quantitative measurements from at least one sensor of the external device. The at least one non-transitory computer readable medium may contain further instructions configured when executed to provide a graphical user interface on the external device, wherein the graphical user interface is configured to receive the at least one qualitative measurement and to provide the at least one qualitative measurement to the first algorithm. The medical device may comprise at least one sensor configured to provide at least one of the quantitative measurements to the first algorithm.

In either of the first or second examples, the system may further comprise an external device configured to allow a patient to adjust the program executed by the medical device, wherein the at least one non-transitory computer readable medium is stored in the external device. The external device may comprise at least one sensor configured to provide at least one of the quantitative measurements to the first algorithm. The external device may comprise a graphical user interface configured to allow the patient to enter the at least one qualitative measurement and to provide the at least one qualitative measurement to the first algorithm. The external device may be further configured to display the determined wellness factor on the graphical user interface. The medical device may comprise at least one sensor configured to provide at least one of the quantitative measurements, and to transmit the at least one of the quantitative measurement to the first algorithm in the external device.

In either of the first or second examples, the at least one non-transitory computer readable medium may be stored in the medical device. The medical device may comprise at least one sensor configured to provide at least one of the quantitative measurements to the first algorithm.

The quantitative measurements may be affected by the symptom. The wellness factor may be indicative of the severity of the symptom.

In either of the first or second examples, the first algorithm may be configured to determine the wellness factor for the patient by correlating the plurality of quantitative measurements to the at least one qualitative measurement. The first algorithm may be configured to estimate a qualitative measurement for each quantitative measurement. The first algorithm may be configured to determine a correlation coefficient between each quantitative measurement and each at least one qualitative measurement. The first algorithm may be configured to determine the wellness factor by weighting the estimated qualitative measurement for at least some of the quantitative measurements using the correlation coefficients for the at least some of the quantitative measurements. The wellness factor may comprise at least some of the estimated qualitative measurements.

In either of the first or second examples, the medical device may comprise an implantable neurostimulator.

In either of the first or second examples, the at least one non-transitory computer readable medium may further contain instructions for a second algorithm, wherein the second algorithm when executed is configured to adjust the program executed by the medical device using the wellness factor. The second algorithm when executed may be further configured to adjust the program executed by the medical device using the wellness factor and using at least one of the plurality of quantitative measurements. The medical device may comprise an implantable neurostimulator configured to execute a stimulation program, and wherein the second algorithm when executed may be configured to adjust an amplitude of the stimulation program. The first algorithm and the second algorithm may be configured to be executed on an external device configured to adjust the program executed by the medical device. The first algorithm may be configured to be executed on an external device configured to adjust the program executed by the medical device, and wherein the second algorithm may be configured to be executed on the medical device.

BRIEF DESCRIPTION OF THE DRAWINGS

FIG. 1 shows an Implantable Pulse Generator (IPG), in accordance with the prior art.

FIG. 2 shows an example of stimulation pulses (waveforms) producible by the IPG or by an External Trial Stimulator (ETS), in accordance with the prior art.

FIGS. 9A and 9B show how the wellness modelling algorithm can be distributed between the external controller and the clinician programmer, while

FIG. 10A shows a stimulation optimization algorithm operable in the IPG or ETS to adjust a stimulation program using the determined wellness factor. FIGS. 10B-10E show various manners in which the wellness modelling algorithm and stimulation optimization algorithm can be distributed between the clinician programmer, the external controller, and the IPG or ETS.

DETAILED DESCRIPTION

Figure 3:
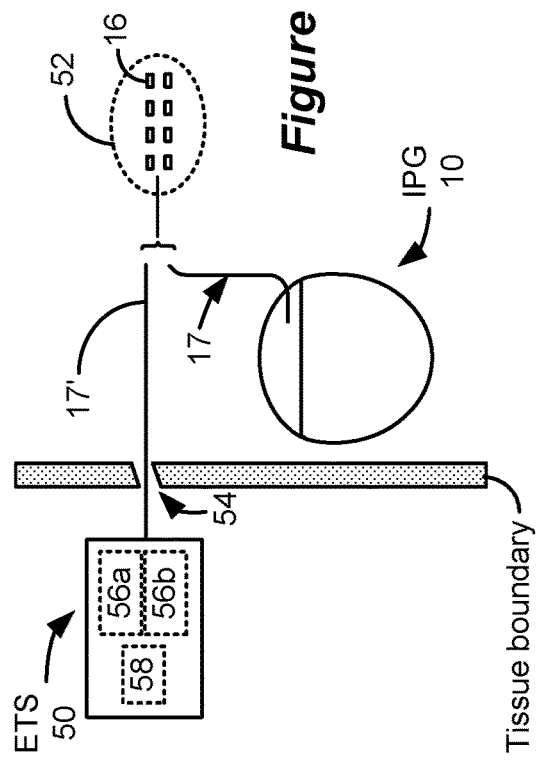
FIG. 3 shows an ETS environment useable to provide stimulation before implantation of an IPG, in accordance with the prior art.

A goal of neurostimulation therapy, whether provided by an implanted IPG or externally by an ETS, is the reduction of unwanted symptoms such as pain, tremor, depression, etc. It is therefore useful for many reasons to measure the effectiveness of such therapies.

Typically the effectiveness of SCS therapy is measured qualitatively. Qualitative measurements rely on subjective input from the patient regarding their perception of how SCS therapy is affecting their symptoms. Many qualitative measurements require the patient to rate or rank symptom severity (e.g. pain). For example, the Numerical Rating Scale (NRS) and the Visual Analogue Scale (VAS) allow an SCS patient to rank pain on a scale of 0 to 10, with 0 denoting no pain and 10 denoting a worst pain imaginable. The Patient Global Impression of Change Scale (PGIC) is similar, but measures the success of SCS therapy relative to the patient's symptoms before receiving their implant. For example, a mid-point ranking of 5 might indicate that SCS therapy has not improved the patient's pain; a 0 might indicate that pain is much improved with therapy; and a 10 might indicate that pain is much worse with therapy. The EQ-5D scale can also be used in the SCS therapy context, and addresses wellness concerns beyond pain. The EQ-5D comprises a questionnaire asking a patient to rank various wellness factors that SCS therapy might be impacting, such as patient mobility, ability to provide self-care, pain or discomfort, anxiety or depression, etc. The ranks for each can then be used to compile a single index of wellness. Other qualitative measurements useful for assessing SCS therapeutic effectiveness also exist, and are not limited to patient assessment of pain. SCS patients may also qualitatively rate the effectiveness of SCS therapy by assessment of depression, anxiety, stress, nausea, numbness, dizziness, weakness, fatigue, etc. Qualitative measurement of such other symptoms may occur using the Montgomery-Asberg Depression Rating Scale (MADRS), the Hamilton Depression Rating Scale (HAM-D), Newcastle Depression Scales, and the Clinical Global Impression Scale (CGI). Tremor can also be qualitatively rated by a patient using numerical and other similar scales. Pain, depression, anxiety, stress, obsessive urges, other psychiatric states, nausea, numbness, dizziness, weakness, fatigue can also be useful in qualitatively assessing the effectiveness of DBS therapy.

Quantitative measurements to gauge the effectiveness of SCS therapy are not known to be in widespread use, but several quantitative measurements of pain exist that could be used to gauge therapy effectiveness in an SCS system. Quantitative measurements rely on objective measurements taken from a patient. Examples of objective measurements that have shown promise as reliable indicators of pain include: brain wave measurements (such as taken from a Electroencephalograph (EEG)); neural response measurements (which may be deduced from Evoked Compound Action Potentials (ECAPs)); patient activity or posture measurements (which may be measured using an accelerometer or other activity sensor); galvanic skin resistance measurements; heart rate, heart rate variability, and/or EKG measurements; patient temperature measurements; sleep data measurements; blood flow measurements (such as taken from a photoplethysmogram (PPG)), biochemical sensor measurements; etc.

Other quantitative measurements may include medication dosing information. For example, an SCS patient may be taking pain medications concurrent with SCS therapy. Because the dosing of pain medication taken should scale inversely with pain, such dosing can be used as a quantitative measurement of pain. The amount of pain medication taken can be measured by automated means, such as by including electrical sensors in each of the patient's pain pills. See Proteus Discover™ by Proteus Digital Health, Inc., as described at http://www.mobihealthnews.com/content/california-hospital-becomes-first-us-prescribe-ingestible-sensors-proteus (Jan. 11, 2016).

Some of these quantitative measurements can be taken by the same SCS IPG or ETS device that provides the therapy. For example, ECAPs can be sensed in an SCS IPG or ETS (see U.S. Provisional Patent Application Ser. No. 62/568,211, filed Oct. 4, 2017), as can heart rate (see U.S. patent application Ser. No. 16/282,130, filed Feb. 21, 2019). Patient posture and activity can be sensed in an SCS IPG (see U.S. Pat. Nos. 9,446,243 and 8,788,055). Other quantitative measurements may be taken using devices or systems independent of the SCS system. For example, brain waves can be measured using an Electroencephalography (EEG) system;

ECAPs can be measured using an Electromyography (EMG) system; blood flow can be measured using a finger probe; patient posture and activity can be measured using an accelerometer in a FitBit™ wearable activity monitor or the patient's cell phone; sleep data can be measured using any of the pieces of equipment used during a Polysomnography analysis (sleep study), or by other activity monitoring devices; etc.

Quantitative measurements to gauge the effectiveness of DBS therapy are also not known to be in widespread use, but similar sensors can provide evidence of effectiveness in a DBS system.

Both qualitative and quantitative measurements have shortcomings when gauging the effectiveness of therapy. Qualitative measurements of effectiveness are inherently suspect because of their subjective nature, and because they lack the precision to provide a fuller indication of therapy effectiveness. For example, in the SCS context, one patient may simply have a low pain tolerance, and may provide (e.g., per NRS) a pain rating of 7, while another patient with a higher pain tolerance might provide a 3. In another example, a patient might indicate prior to receiving SCS therapy that his pain is a 7, and that after receiving SCS therapy his pain is a 6. It would not seem in this instance that SCS therapy has been significantly effective for the patient. However, despite these pain rankings, the patient may be receiving significant benefit from the therapy. For example, prior to receiving therapy the patient may report that a large portion of his back hurt, thus limiting his activity. After receiving therapy, the patient may report that only a small portion of his back hurts (albeit still significantly), which nonetheless allows him to be significantly more active than before. The qualitative measurement of pain is in this example too simple to tell the entire story of patient wellness.

Quantitative measurements may also not provide an accurate indication of the effectiveness of therapy. Assume two patients each reporting a qualitative pain score of 6 prior to receiving SCS therapy, and after receiving therapy that the activity of each is monitored (using an IPG-based or an external accelerometer for example) as a quantitative measurement of SCS efficacy. The first patient might report that his pain level is down to a 3 after receiving therapy. This first patient may however also be sedentary even though his pain has been relieved, and thus the quantitative measurement of his activity may be very low. While therapy is effective for this patient, such effectiveness is not well reflected in the quantitative measurement of activity. The second patient might report that her pain level is still at a 6 after receiving therapy, suggesting that therapy is not effective. This second patient may however be very active after receiving therapy. In effect, this second patient may have chosen to trade pain relief for activity. That is, the therapy may be providing good relief, and allows the patient to increase his activity level, despite no change in the patient's pain score. Thus, while activity may generally comprise a sensible quantitative measurement to gauge the effectiveness of SCS therapy, it is not reliable in all cases and may not be effective for all patients.

It is therefore difficult to universally establish qualitative or quantitative measurements that can gauge the effectiveness of therapy for all patients. In recognition of this fact, a system is disclosed which allows for modelling the wellness of a given IPG patient. The modelling, embodied in an algorithm, uses one or more qualitative measurements and one or more quantitative measurements taken from the patient. The algorithm correlates the qualitative measurements to the various quantitative measurements to eventually, over time, learn which quantitative measurements best correlate to the qualitative measurements provided by the patient. The algorithm can then using current quantitative measurements predict a wellness factor or score for the patient, which is preferably weighted to favor the quantitative measurements that best correlate to that patient's qualitative assessment of therapy effectiveness. Additionally, the wellness factor may be used to adjust the stimulation program that the IPG device provides to the patient.

Figure 4:
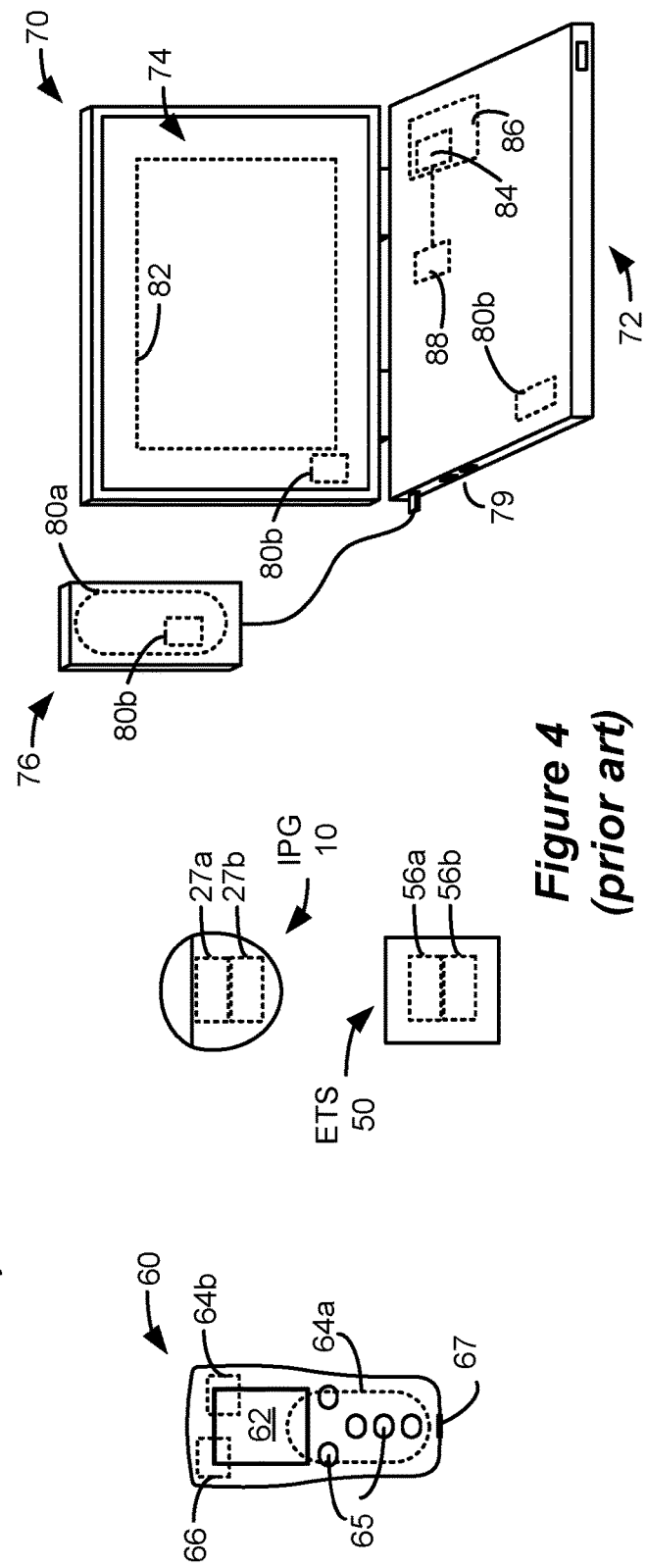
FIG. 4 shows a patient external controller and a clinician programmer capable of communicating with and programming stimulation in an IPG or ETS, in accordance with the prior art.
Figure 5:
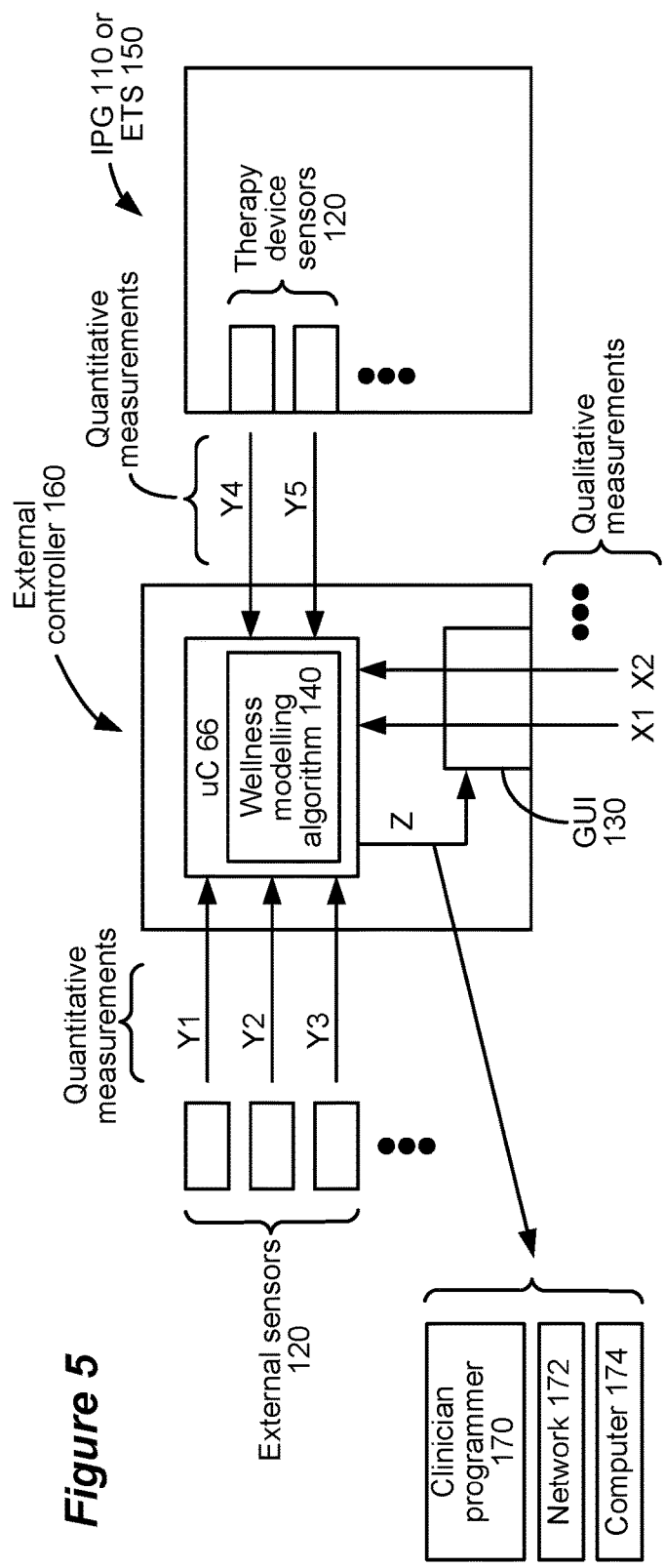
FIG. 5 shows embodiment of a wellness modelling algorithm in a patient external controller that receives qualitative and quantitative measurements of a patient's symptoms, and determines a wellness factor.

FIG. 5 shows an example of a system in which the wellness modelling algorithm 140 can be employed. In this example, the wellness modelling algorithm 140, and its computation of a wellness factor Z for the patient, is embodied in an external controller 160, which may generally be similar to the patient external controller 60 described earlier (FIG. 4). However, embodying the algorithm 140 in a patient external controller 160 is not strictly necessary, as described further below. Preferably the wellness modelling algorithm 140 operates as firmware, software or microcode operable in the control circuitry 66 of the external controller 160 as described earlier.

Figure 8:
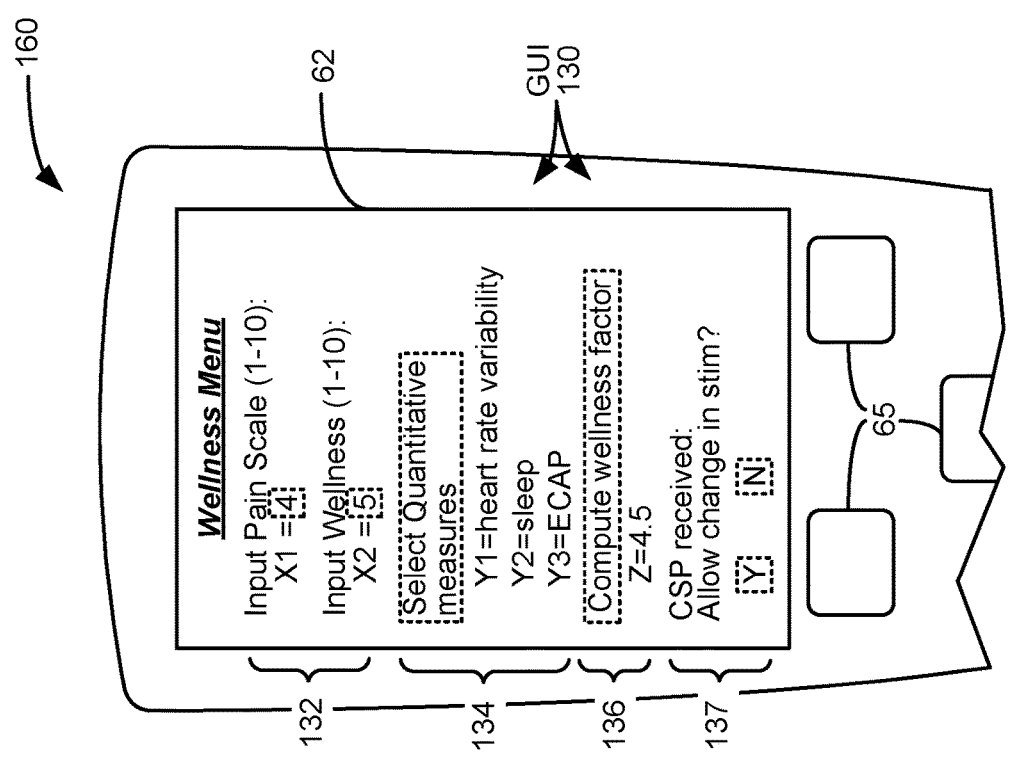
FIG. 8 shows a Graphical User Interface operable on the external controller or the clinician programmer to display and enter various data relevant to the wellness modelling algorithm.

The wellness modelling algorithm 140 receives one or more qualitative measurements X1, X2, etc. In the example shown, a patient can enter such qualitative measurements using the Graphical User Interface (GUI) 130 of the external controller 160, as shown in FIG. 8. GUI 130 shows a "Wellness Menu" on screen 62, which may have been entered by selecting this menu previously in the GUI 130. The Wellness Menu allows the patient, using interface elements such as buttons 65, to input one or more qualitative measurements at inputs 132. In this example, a first qualitative measurement X1 comprises a pain scale, such as the NRS scale described earlier. A second qualitative measurement X2 comprises a general wellness scale, which again may range from 1-10, and which may generally inquire as to the patient's well being, as opposed to their pain per se. More or different qualitative measurements could be input as well. The patient may enter such qualitative measurement inputs 132 at any time, and on any particular time scale. It might be expected that the patient might enter such qualitative measurements once or twice a day, but as this depends on the patient, such regularity cannot be guaranteed.

Returning to FIG. 5, the wellness modelling algorithm 140 also receives one or more quantitative measurements of pain, i.e., Y1, Y2, etc. As noted earlier, such quantitative measurements can come from various sensors taking measurements from the patient, and as described earlier can comprise sensors within the IPG 110 or ETS 150 (therapy sensors 120), or sensors separate from such therapy devices (external sensors 130). Quantitative measurements taken from therapy device sensors 120 would preferably be wirelessly communicated from the IPG 110 or ETS 150 to the external controller 160, while quantitative measurements taken from external sensors 120 could be wirelessly transmitted or sent to the external controller 160 via a wire or cable. For example, the external sensors 120 could connect to a port 67 (FIG. 3) on the external controller 160. Although not shown, external sensors 120 can also be contained within the external controller 160 itself. For example, the external controller 160 may have an accelerometer capable of monitoring patient activity as a quantitative measurement. External sensors 120 may also more generally comprise a source of other quantifiable measurements relevant to therapeutic effectiveness. For example, drug dosing information may be said to come from an external sensor 120, even if information does not comes from a traditional sensor that measures the patient. In this example, drug dosing information may be entered by the patient into a computer acting as a sensor 120.

Returning again to FIG. 8, the quantitative measurements that the wellness modelling algorithm 140 uses may be specified or reviewed by the patient at interface aspect 134. For example, the patient may select a link at aspect 134 that instructs the patient how to connect ("handshake") the relevant sensors 120 or 130 to the external controller 160, be they wired or wireless. Aspect 134 may also show the quantitative measurements the algorithm 140 will use after they have been selected. In the example shown, the algorithm 140 will use three different quantitative measurements: Y1, indicative of heart rate variability; Y2, indicative of a sleep-related parameter, and Y3, indicative of the magnitude of neural response to stimulation (e.g., ECAP response).

Returning to FIG. 5, the wellness modelling algorithm 140 receives the qualitative measurement(s) (Xi) and the quantitative measurement(s) (Yi), and uses them to compute a wellness factor Z. Wellness factor Z may be viewable on the GUI 130 of the external controller 160 in the Wellness Menu, as shown at interface aspect 136 in FIG. 8. As shown in FIG. 5, the wellness factor Z may also be communicated to other external devices, such as a clinician programmer 170, which may be similar to the clinician programmer 70 described earlier (FIG. 4), and which may also be used to render a GUI similar to that shown in FIG. 8. Communication between the external controller 160 and the clinician programmer 170 can occur wirelessly as described earlier (FIG. 4), or by a wired connection. There can be benefit to a clinician's review of the wellness factor Z, and the wellness modeling algorithm 140 can send other data to the clinician programmer as well, as explained further below. Wellness factor Z can also be communicated to a network 172, such as the Internet, making it reviewable on a computer 174 connected to the network 172. For simplicity, further reference to the clinician programmer 170 should be understood to include such other computers 174 and networks 172.

It is preferred that the qualitative measurement(s) (Xi) and the quantitative measurement(s) (Yi) are received at the patient external controller 160. This is preferred because the external controller 160 is device is generally proximate to (e.g., carried by) the patient, and hence proximate to the sensors 120 and 130 which are also generally proximate to the patient, such that the sensors can easily communicate such measurements to the external controller 160. This allows measurements to be taken and the wellness modelling algorithm 140 to operate on a continual basis, and preferably as the patient goes about his daily activities. However, and although not shown, the qualitative measurement(s) (Xi) and the quantitative measurement(s) (Yi) can be received at other external devices such as the clinician programmer 170 or even the IPG 100 or ETS 150 itself. As discussed further below, the wellness modelling algorithm 140 may be embodied in these other devices.

Figure 6:
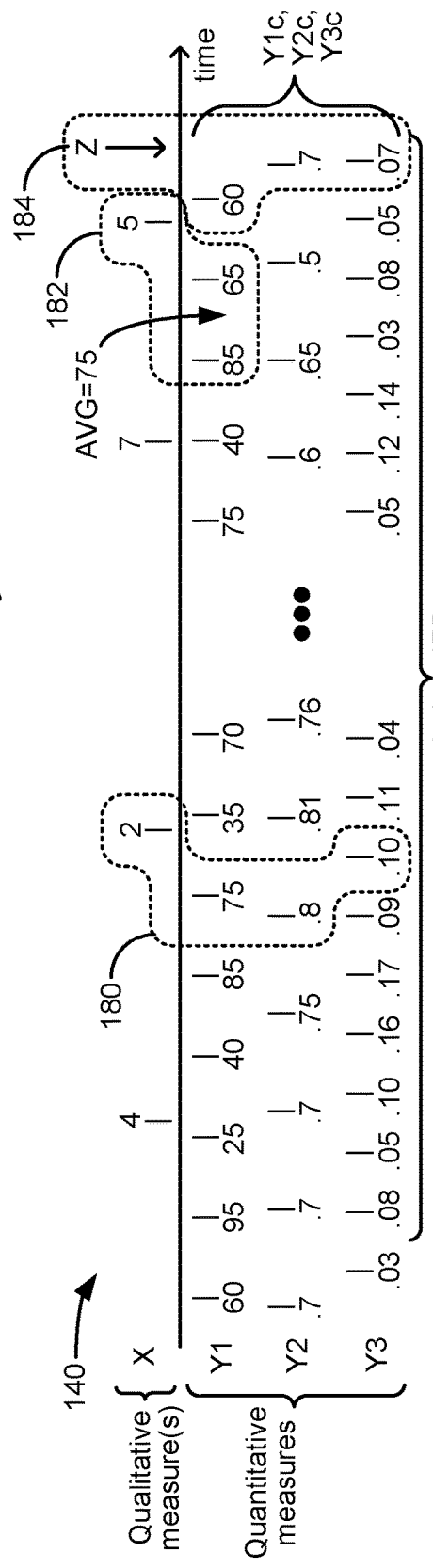
FIG. 6 shows an example of qualitative and quantitative measurements being received by the wellness modelling algorithm.

FIG. 6 shows an example of qualitative and quantitative measurements as received by the wellness modelling algorithm 140. In this example, three quantitative measurements Y1, Y2 and Y3 are used. These quantitative measurements may comprise any of the quantitative measurements described earlier, and may be taken from the therapy device sensor 120 or the external sensors 130. Notice that the sensors report their measurement data to the algorithm 140 at different rates: Y3 reports more frequently than does Y1, and Y1 reports more frequently than does Y2. Such variability in measurement reporting frequency may depend on the sensors being used. The algorithm 140 may also receive or process (e.g., average) reported quantitative measurements at a constant rate. Although the quantitative measurements Yi are shown as periodic, this is not required, and instead they can be reported to the algorithm 140 at random times. Furthermore, some sensors may only be worn or used by the patient at certain times (e.g., during the day), meaning that those sensors would not report measurements at other times (e.g., at night).

Notice that the reported quantitative measurements Yi may differ in their magnitudes. This depends on the sensor 120 or 130 used, and the quantities they measure. Y1, comprising heart rate variability for example, may vary from 0-100 beats per minute. Y2 may comprise some quantitative sleep parameter, which happens to vary from 0 to 1. Y3 may comprise a measured magnitude of ECAP neural responses, which may range from 0 to 0.2 Volts. Such variability in the magnitude of the reported quantitative measurements Yi will not affect the operation of the wellness modelling algorithm 140. However, if necessary or useful, the various quantitative measurements Yi can be normalized by the algorithm 140. For example, to arrive at quantitative measurements that only vary from 0 to 1, Y1's measurements (ranging from 0 to 100) can be scaled by a factor of 0.01; Y3's measurements (ranging from 0 to 0.2) can be scaled by 5; Y2 (which already ranges from 0 to 1) may simply not be scaled (i.e., scaled by a factor of 1).

In the example of FIG. 6, only one qualitative measurement X is used, although as mentioned above a plurality of qualitative measurements could also be processed by the wellness modelling algorithm 140. Qualitative measurement X may comprise for example a NRS pain score, and as described above can be entered by the patient into the GUI 130 of their external controller 160 (FIG. 8, 132). Even if the patient is instructed by his clinician to enter such qualitative measurements X on a schedule (e.g., twice a day), notice that such qualitative measurements X may be entered at random times. Further, as mentioned above, it might be expected that a patient would enter qualitative measurements X much less frequently than the quantitative measurements Yi would be reported. For example, while qualitative measurements X might be entered on a time scale of hours or days, quantitative measurements Yi might be reported on a scale of seconds or minutes.

Preferably, the wellness modelling algorithm 140 will store each qualitative (Xi) and quantitative (Yi) measurement it receives along with a timestamp so that the algorithm 140 can know at which time each data point is received. Associating each measurement with a timestamp can be useful for many reasons, but in one example, the algorithm 140 when performing its calculations may ignore measurements that fall outside of a window 175 of time. In other words, the algorithm may ignore measurements that are too old to be useful. This is sensible, because a patient's circumstances can change over time, making older data less reliable to consider. For example, the patient may over time have significantly changed the stimulation program the IPG 110 or ETS 150 is running, or may have healed or formed scar tissue, or may have reduced the level of pain medication he is taking, etc. In one example, window 175 may comprise a time period of a month, and thus the wellness modelling algorithm 140 will discard any data with a time stamp older than this duration.

The wellness modelling algorithm 140 seeks to determine how well each quantitative measurement Y1, Y2, and Y3 correlates to the qualitative measurement X entered by the patient, which then allows the algorithm to compute a wellness factor Z. Preferably, wellness factor Z is determined or weighted to favor the quantitative measurements that best correlate to X, as discussed in detail below. It should be noted that that are several manners of establishing correlations between the quantitative measurements Y1, Y2, and Y3 and qualitative measurement X. However, for purposes of a simple illustration, it is assumed that the wellness modelling algorithm 140 will determine correlation using a linear regression analysis.

Figure 7:
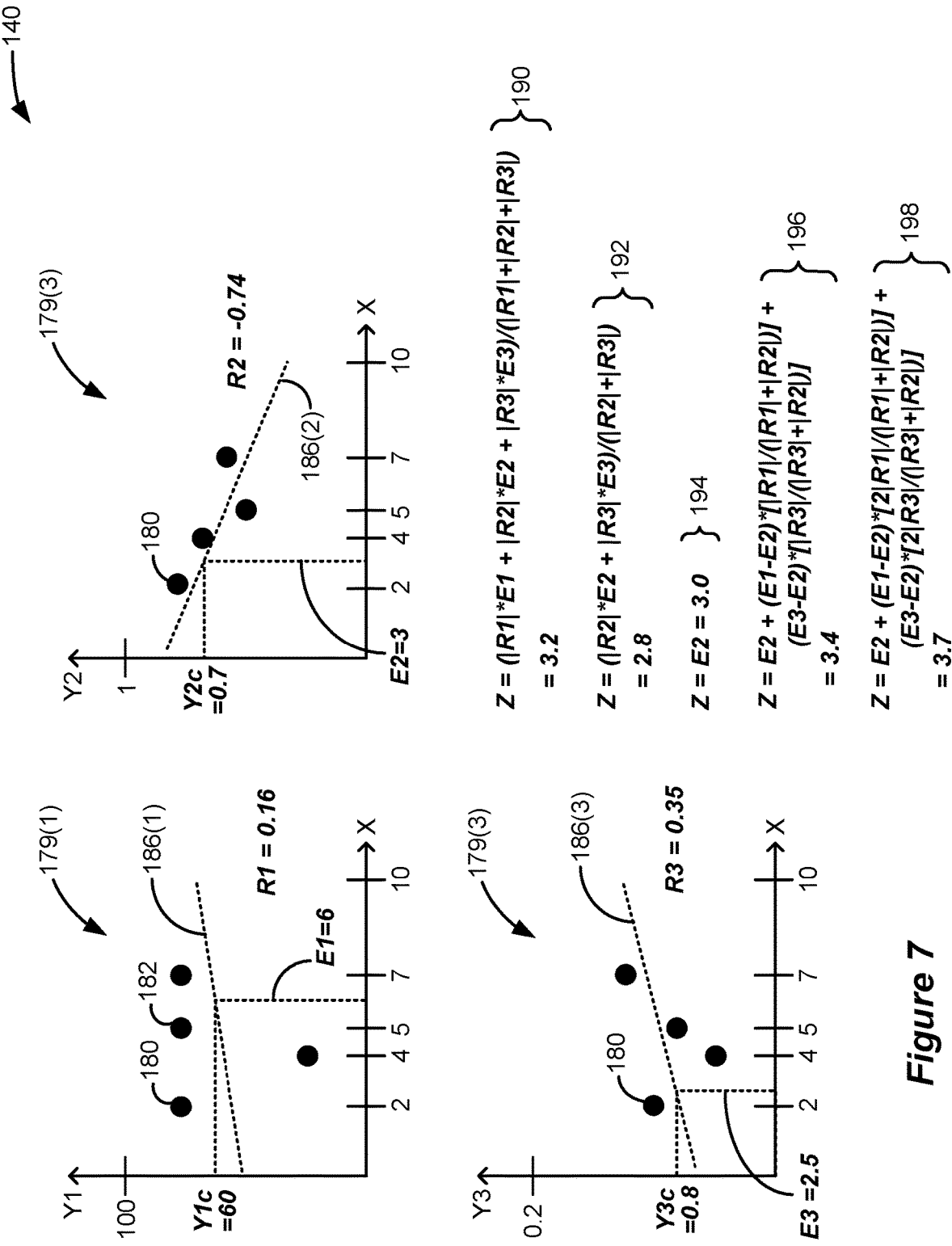
FIG. 7 shows an example by which the quantitative measurements can be correlated with a single qualitative measurement, and shows determination of the wellness factor using such correlated data.

FIG. 7 shows graphs correlating X with Y1 (179(1)), with Y2 (179(2)), and with Y3 (179(3)). The data points in each graph are preferably only determined based on qualitative and quantitative measurements falling within window 175, and such data points can be determined in different ways. Consider data points 180, each associated with a qualitative measurement X=2. As shown in FIG. 6, these data points 180 can be established by determining the value of the quantitative measurements Y1=75, Y2=0.8 and Y3=0.10 that immediately preceded the entry by the patient of X=2. Therefore, graph 179(1) includes a data point 180 at (2, 75), graph 197(2) includes a data point 180 at (2, 0.8), and graph 179(3) includes a data point 180 at (2, 0.10).

The data points in graphs 179 may be determined in different manners. For example, data point 182 in graph 179(1), occurring at qualitative measurement X=5, is established by associating this qualitative measurement with the average of the two preceding quantitative measurements (Y1=85 and 65). Thus, graph 179(1) includes a data point 180 at (5, 75). In other words, some number of quantitative measurements can be averaged and associated with each qualitative measurement to determine the data points in the graphs, such as a certain number of preceding quantitative measurements, preceding quantitative measurements over a certain time period, all preceding quantitative measurements since a last qualitative measurement, etc. A qualitative measurement can likewise be associated with one or more quantitative measurements that are subsequent to the qualitative measurement, or quantitative measurements that are both preceding and subsequent.

Returning to FIG. 7, once the data points in each graph 179(1)-(3) are established by the wellness modelling algorithm 140, the algorithm 140 can determine a regression line 186(1)-(3) for each. Regression lines 186(1)-(3) in this example are determined using linear regression, such as by a least-squares linear regression, although other line-fitting techniques can be used, including non-linear fitting techniques.

Also determined by the algorithm 140 as part of its regression analysis is a correlation coefficient Ri that quantifies how well each quantitative measurement Yi is correlated to the qualitative measurement X (and thus how well each regression line 186 fits the data points). Correlation coefficient Ri in these examples ranges from −1 (a perfect negative correlation) to +1 (a perfect positive correlation), with a value of zero denoting no correlation whatsoever. Thus, it is seen that correlation coefficient R1=0.16 for graph 179(1) suggests almost no correlation between quantitative measurement Y1 (e.g., heart rate variability) and qualitative measurement X for the patient in question. By contrast, correlation coefficient R2=−0.74 for graph 179(2) suggests a strong (negative) correlation between quantitative measurement Y2 (e.g., a sleep parameter) and qualitative measurement X for the patient in question. The correlation coefficient R3=0.35 for graph 179(1) suggests a weak (positive) correlation between quantitative measurement Y3 (e.g., magnitude of ECAP neural response) and qualitative measurement X for the patient in question.

To summarize, the wellness modelling algorithm 140 has to this point determined that quantitative measurement Y2 best correlates to this patient's subjective sense of therapy effectiveness as reflected by qualitative measurement X, followed by quantitative measurement Y3, and followed further by quantitative measurement Y1. Note that this is not a universal determination that Y2 correlates well and Y1 correlates poorly for all patients, but is instead a conclusion the wellness modelling algorithm 140 reaches that is specific to the patient in question and at a particular point in time. For example, the wellness modelling algorithm 140 might determine for another patient that quantitative measurement Y1 best correlates to their qualitative measurement of X. In other words, the wellness modelling algorithm 140 is specific to, and learns using measurements from, a specific patient, which increases its reliability.

With the correlations between the quantitative measurements Yi and the qualitative measurements X established, the wellness modelling algorithm 140 may now determine a wellness factor Z. The wellness factor Z can be determined based on reported quantitative measurements alone. Preferably, the wellness factor is determined using recently-received quantitative measurements, shown in FIG. 6 as data points 184. Data points 184 comprise the current (or immediately preceding) reported values for quantitative measurements Y1, Y2, and Y3 (Y1$c$, Y2$c$, and Y3$c$, with subscript 'c' denoting 'current'). However, as before, current quantitative measurements Yi$c$ can also comprise an average of some number of preceding or subsequent values for Yi. Using just immediately-preceding single data points for each as shown in FIG. 6, it is seen that Y1$c$=60, Y2$c$=0.7, and Y3$c$=0.07.

The wellness modelling algorithm 140 can then use the regression lines 186(1), 186(2), and 186(3) to estimate a qualitative measurement E1, E2, E3 for each. As FIG. 7 shows, this comprises solving each regression line 186($i$) for Ei at the given Yi$c$. In the example shown, the following estimated qualitative measurements result: E1=6, E2=3, and E3=2.5. Generally speaking, each of these values Ei are an estimate of the qualitative measurement X that would be expected given the current quantitative measurement Yi$c$.

The wellness modelling algorithm 140 then uses the estimated qualitative measurements Ei to arrive at a single wellness factor Z. Preferably, the wellness factor Z attributes more significance or weight to estimated qualitative measurements Ei having higher correlation coefficients Ri. This can be achieved in different manners. In example 190, each estimated value Ei is weighted by multiplying it by the absolute value of its correlation coefficient Ri, and these products are summed (i.e., |R1|*E1+|R2|*E2+|R3|*E3). This ensures that the estimated value E2 (corresponding to the highest-correlated quantitative measurement Y2 for the patient) is given more significance in the overall sum of the products, while E1 (corresponding to the lowest-correlated quantitative measurement Y1) contributes little to the sum. The sum of the products can be divided by the sum of all of the correlation coefficients (i.e., by |R1|+|R2|+|R3|) to normalize the result. This results in example 190 in the calculation of a wellness factor Z=3.2. Notice that this value is sensibly close to the estimated qualitative measurement E2=3 for the most highly-correlated quantitative measurement Y2.

Example 192 is similar to example 190, but simply omits from the wellness factor Z determination the least-relevant estimated qualitative measurement E1, that is, the estimate corresponding to the lowest-correlated quantitative measurement Y1. Thus, only estimates E2 and E3 are multiplied by their correlation coefficients R2 and R3 (i.e., |R2|*E2+ |R3|*E3), and normalized (divided by |R2|+|R3|). A wellness factor of Z=2.8 results, which is sensibly between the estimated values E2 and E3 corresponding to the remaining quantitative measurements Y2 and Y3. Exclusion of an estimated qualitative measurement Ei from the wellness factor Z determination can be made in different ways. For example, the least relevant (worst correlated) can be discarded as in example 192, or the two least relevant can be discarded, etc. Also, exclusion of an estimated qualitative measurement can be determined based on a cut-off: for example, all estimates Ei associated with a correlation coefficient Ri less than 0.4 could be excluded as too poorly correlated to be useful, etc. Example 192 further illustrates that, over time as statistical relevance becomes clear, quantitative measurements like Y1 that correlate poorly with the patient's qualitative measurement X can simply be dispensed with, i.e., the patient will no longer need to wear sensors that take those measurements.

Example 194 determines wellness factor simply as the estimated qualitative measurement E2 of the quantitative measure Y2 that best correlates to the input qualitative measure X. Again, this suggests that quantitative measurements Y1 and Y3 can simply be dispensed with. Instead, the patient may then only need a sensor to quantitatively measure Y2, which can then be used alone to determine the wellness factor Z. In this regard, notice that implementation of the wellness modeling algorithm 140 does not necessarily require the use of more than one quantitative measures Yi. Instead, only a single quantitative measure Y may be used to determine wellness factor Z, particularly if that single quantitative measurement Y has been learned by the algorithm 140 to have significant correlation with qualitative measure X.

Example 196 shows another method by which the wellness modelling algorithm 140 can determine wellness factor Z. In this example, the estimated qualitative measurement (E2) corresponding to the highest-correlated quantitative measurement (Y2) is used as the basis for the calculation, and thus comprise the first factor in the sum. However, that estimated value E2 is pulled higher or lower based on the other estimated values (E1 and E3) with a strength dependent on their respective correlation coefficients (|R1| and |R3|). For example, a difference E1-E2 can be calculated. Because this difference is positive (6−3=3), E1 will pull the wellness factor Z higher from its base value E2, in accordance with a weighting as set by their correlation coefficients (i.e., +(E1−E2)*[|R1|/(|R1|+|R2|)]). Likewise, a difference E3-E2 can be calculated. Because this difference is negative (3−2.5=−0.5), E3 will pull the wellness factor Z lower from its base value E2, again in weighted fashion (i.e., +(E3−E2) *[|R3|/(|R3|+|R2|)]). The result is a wellness factor of Z=3.4.

Example 198 shows another method for determining wellness factor Z that is similar to example 196, but multiplies |R1| and |R3| by 2 in the weighting factors. In this way, as |R1| or |R3| approaches |R2|, the weighting factors 2|R1|/(|R1|+|R2|)] and 2|R3|/(|R3|+|R2|)] will approach 1.

Again, there are many ways wellness modelling algorithm 140 can determine wellness factor Z after determining the relevance of each of the quantitative measurements Yi for the patient, and examples 190-198 should be understood as non-limiting.

In the examples shown to this point, notice that the wellness factor Z will vary, or can be constrained to vary, in the same range as the qualitative measurement X. That is, just as qualitative measurement X can range from 0 to 10, so too can Z range from 0 to 10. However, this is not strictly necessary, and the range of wellness factor Z can differ from the range allowed for the qualitative measurement X. Wellness factor Z is shown in the illustrated example to increase when wellness decreases, but again this is not necessary and instead an increasing Z can indicate increasing wellness. Wellness factor Z may be viewable on the GUI 130 of the external controller 160 in the Wellness Menu, as shown at interface aspect 136 in FIG. 8.

Although not illustrated, it should be understood as mentioned earlier that more than one qualitative measurement— e.g., X1 and X2—can be used in the wellness modeling algorithm. In that circumstance, the correlation of each quantitative measurement Yi can be correlated to both X1 and X2, with the wellness factor Z computed as a function of such correlations, and again preferably favoring the quantitative measure with the best correlation. Such multi-variable correlation techniques are well known and not illustrated for simplicity.

Further, the wellness modelling algorithm 140 may employ other techniques to compute the wellness factor. For example, the qualitative measurement Xi and the quantitative measurements Yi can be analyzed and a wellness factor Z determined using weighted linear techniques, other linear or non-linear optimization techniques, principal component analysis techniques, artificial neural network techniques, support vector machine method techniques, other machine learning or artificial intelligence (AI) techniques, etc.

Still further, and although not depicted in the examples 190-198 of FIG. 7, the wellness factor Z may also be determined, at least in part, as a function of the qualitative measure X, for example by using X as last entered by the patient X and particularly if X was relatively recently entered by the patient. For example, X may be assigned a higher weight in the calculation of Z if X was entered recently in time.

Preferably, the wellness modelling algorithm 140 will determine the wellness factor Z as a function of time. It may determine Z with a set period, such as every ten minutes. Or, it may determine Z any time a new qualitative measurement Xi or quantitative measurement Yi is received. Beneficially, and assuming sensors 120 and 130 can report quantitative measurements Yi at a high rate, the wellness modelling algorithm 140 can compute Z on a much shorter time scale than the patient might otherwise enter their assessment of wellness via the qualitative measurement Xi. This allows the algorithm 140 to compute the wellness factor Z even during periods when the patient has not (recently) entered any qualitative measurements Yi, thus providing a generally continuous indication of patient wellness. The wellness factor Z may also be automatically produced at the patient's request, such as by selecting the "compute" input of interface aspect 136 (FIG. 8).

In another example, the wellness modelling algorithm 140 can compute wellness factor Z as a function of the received quantitative measurements Yi, and in particular as a function of the patient's current quantitative measurements Yic. This may be in addition to also computing the wellness factor Z as a function of the qualitative measurements Xi via their estimations Ei.

It should be understood that the determined wellness factor Z can be indicative of the status of the patient as gauged by the qualitative measurements Xi. Such patient status can comprise a qualitative measurement of a primary symptom that the medical device is configured to directly treat. For example, in an SCS system designed to treat a primary symptom of pain, at least one qualitative measurement X can include a patient's rating of pain, using the various pain scales described earlier. The wellness factor Z that the wellness modelling algorithm 140 determines will then be indicative of the severity of patient pain. Patient status can also comprise a qualitative measurement of secondary symptoms related to a patient's primary symptom. For example, pain in an SCS patient may be causing depression, anxiety, or other secondary symptoms. By providing at least one qualitative measurement X rating a secondary symptom (e.g., depression), the wellness modeling algorithm 140 will provide a wellness factor indicative of the severity of that secondary symptom. Providing qualitative measurements Xi ranking both pain and depression will produce a wellness factor Z indicative of both of these statuses, etc. The status of the patient need not comprise a symptom per se, but may more generally comprise some other measure of a patient's wellbeing. For example, the patient could provide as a qualitative measurement information rating their happiness, activity level (here as a qualitative measurement, although activity level can also comprise a quantitative measurement as described earlier), ability to work, or any other relevant status that therapy might effect. In such a case, the wellness factor Z comprises a means of quantifying such statuses.

If the wellness factor Z is computed as a function of the received quantitative measurements Yi, wellness factor Z can also be indicative of that particular quantitative measure at least in part. For example, wellness factor Z might in this example be indicative of both pain as a qualitative measurement X and heart rate as a quantitative measure Y.

Figure 9A:
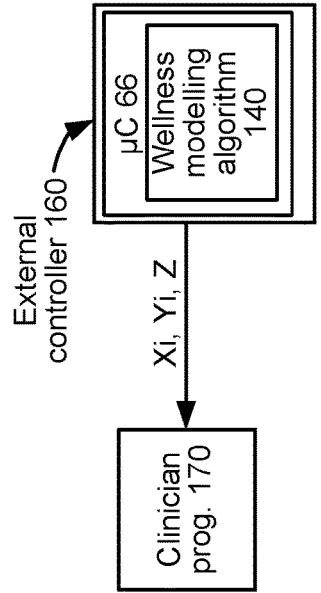
Figure 9B:
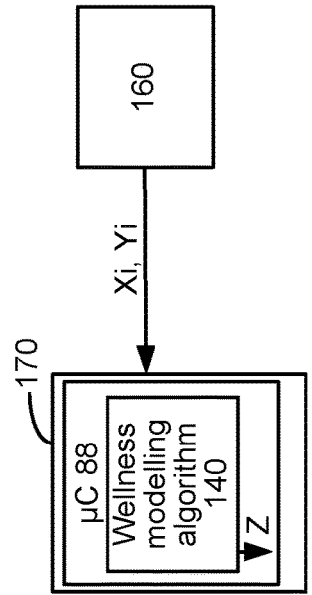

The wellness modelling algorithm 140 may implicate other parts of the system beyond the patient external controller 160. For example, FIGS. 9A and 9B shows two manners in which the wellness modeling algorithm 140 can communicate with, or be distributed between, the external controller 160 and the clinician programmer 170 (which again can comprise other networks 172 or computer 174; FIG. 5). In FIG. 9A, the wellness modelling algorithm 140 resides in the external controller 160, but can communicate relevant data with the clinician programmer 170. In this example, the wellness modelling algorithm 140 computes the wellness factor Z at the external controller 160, but transmits the computed wellness factor Z to the clinician programmer 170. The external controller 160 may also transmit the qualitative measurements Xi entered by the patient and quantitative measurements Yi received from the sensors 120 and 130 (not shown).

Alternatively, the wellness modelling algorithm 140 may be embodied in the clinician programmer 170, as shown in FIG. 9B. Preferably the wellness modelling algorithm 140 comprises firmware, software, or microcode operable in the clinician programmer 170's control circuitry 88 as described earlier. In this example, the external controller 160 preferably collects the qualitative measurements Xi and the quantitative measurements Yi, and then transmits them to the clinician programmer 170, although the clinician programmer 170 can also receive Xi and Yi directly (not shown). The wellness modelling algorithm 140 at the clinician programmer can then determine the wellness factor Z from the data Xi and Yi.

In short, the wellness modelling algorithm 140 can be split between the external controller 160 and the clinician programmer 170, with any relevant data transferred from one to the other. In another example, once the clinician programmer 170 has computed wellness factor Z, Z may be transmitted from the clinician programmer to the external controller 160 so that Z can be reviewed by the patient (FIG. 8, 136).

Figure 9C:
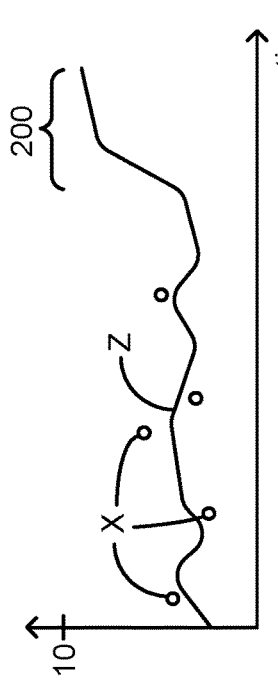
FIG. 9C shows the wellness factor plotted as a function of time.

In either case, it can be useful to have the wellness factor Z, and measurements Xi and Yi, at the clinician programmer 170. This can allows for example the clinician to ensure that the sensors 120 and 130 are working properly—i.e., that the values received for qualitative measurements Yi are appropriate. Reviewing wellness factor Z can also be clinically useful. Assume as shown in the graph of FIG. 9C that the clinician programmer 170 is used to graph wellness factor Z as a function of time, and to present these results on its user interface. The clinician may notice that wellness factor Z has been relatively low and stable for a period of time, but recently (200) has increased. It may be useful in that circumstance for the clinician to reach out to the patient to determine the reason or to suggest modifications to SCS therapy. For example, perhaps the patient would benefit from adjusting the stimulation program the IPG 110 or ETS 150 is running. Note that reaching out to the patient may be especially useful if the patient hasn't recently entered qualitative measurements X which would otherwise indicate the patient's qualitative assessment of their wellness. The graph of FIG. 9C could be provided on the user interface of the external controller 160 as well, and could be graphed to include the wellness factor Z, and either or both of the qualitative measurements Xi and the quantitative measurements Yi.

The wellness modelling algorithm 140 may also be distributed between the external controller 160 and the IPG 110 or ETS 150 that provides SCS therapy. Furthermore, the wellness modelling algorithm 140 may be used to control the stimulation program (SP) that the IPG 110 or ETS 150 is running in a closed loop fashion. For example, in FIG. 10A, the wellness modelling algorithm 140 operates within the control circuitry 210 of the IPG 110 or ETS 150. Control circuitry 210 may comprise a microcontroller, and may be similar to the control circuitries 66 and 88 described earlier. Control circuitry 210 may also comprise a part of, or communicate with one or more Application Specific Integrated Circuits (ASICs), as described in U.S. Patent Application Publications 2012/0095529, 2012/0092031, and 2012/0095519. Such ASIC(s) may include the stimulation circuitry 28 and 58 in the IPG 110 or ETS 150.

The algorithm 140 receives qualitative measurements Xi that the patient has entered into his external controller 160, preferably wirelessly as described previously (FIG. 4) although a wired connection could also be used between the external controller 160 and the ETS 150. Likewise, the external controller 160 can transmit to the IPG 110 or ETS 150 qualitative measurements Yi that it has received from external sensors 130 (FIG. 5). Although not shown in FIG. 10A, it should be understood that the algorithm 140 can also receive quantitative measurements Yi from any therapy sensors 120 (FIG. 5) embodied in the IPG 110 or ETS 150. As before, the wellness modelling algorithm 140 can compute a wellness factor Z.

The wellness factor Z can in turn be used to adjust the stimulation program (SP) the IPG 110 or ETS 150 is executing, thus allowing the wellness factor Z to be used as a means of closed loop control. In this regard, the wellness factor Z can be reported to stimulation programming control circuitry 220 within the control circuitry 210 that is used to generate and send the stimulation program to the stimulation circuitry 28 or 58 in the IPG 110 or ETS 150. Normally the circuitry 220 receives the stimulation program or adjustments thereto from the external devices 160 and 170, and formats the data in a manner interpretable by the stimulation circuitry 28 or 58 in the IPG 110 or ETS 150. The stimulation circuitry 28/58 as described earlier can then form stimulation with the prescribed stimulation parameters (e.g., amplitude, frequency, pulse width, electrode polarity) at the electrodes 16 selected for stimulation.

The wellness factor Z can be used to adjust one or more of the stimulation program's parameters, or to pick a wholly new stimulation program to execute through use of a stimulation optimization algorithm 222. In the example shown, the stimulation optimization algorithm 222 is embodied in the stimulation programming control circuitry 220, although it could reside elsewhere. Stimulation optimization algorithm 222 can also comprise part of the wellness modelling algorithm 140, although it is shown separately for ease of illustration.

As shown in FIG. 10A, the stimulation optimization algorithm 222 can assess wellness factor Z, and if not optimal can change the stimulation program otherwise prescribed for the patient. For example, and assuming a high value for Z indicates poor wellness, the stimulation optimization algorithm 222 can compare Z to a threshold, and if above that threshold, can increase the amplitude of the stimulation program in the hope that increased amplitude will better mask the patient's symptoms (e.g., pain). Algorithm 222 can also more generally scale the amplitude with the wellness factor Z, or may change other stimulation parameters. Algorithm 222 may also choose a new stimulation program for the patient. If wellness factor Z is optimal, the algorithm 222 may simply allow the prescribe stimulation program to be executed by the stimulation circuitry 28 or 58. Note that assessment of the wellness factor Z (223) may occur over some period of time before the stimulation optimization algorithm 222 will indicate that stimulation might be adjusted. This allows the wellness modelling algorithm 140 time to establish reasonable correlations and provide a reliable value for the wellness factor Z as discussed previously, or may similarly allow the stimulation optimization algorithm 222 time to draw its necessary correlations.

The manner in which the stimulation optimization algorithm 222 can adjust the stimulation program given Z can be more complex. For example, the circuitry 222 can over time establish a correlation between the stimulation program (or its parameters) and Z, to determine what programs or parameters have an effect on Z so that the stimulation program can be automatically changed to try and adjust Z to an optimal value. This is particularly useful because while the stimulation program can be changed as a function of Z, it can also be changed by the patient or the clinician using external devices 160 or 170, and so algorithm 222 can over time start to learn a correlation between stimulation programs or parameters and Z.

In another example, the stimulation optimization algorithm 222 can receive quantitative measurements Yi, and in particular can receive the patient's current quantitative measurements Yic, as shown in the dotted-lines arrow in FIG. 10A. This allows the algorithm 222 to understand a patient's current or recent physical state in additional to the estimated wellness factor Z. The algorithm 222 can then adjust the stimulation program as a function of both Z and quantitative measurements Yic. As with Z, Yi can be correlated with different stimulation programs or stimulation parameters, which can then be used by algorithm 222 to adjust stimulation, and hopefully optimize Z, for the patient's current state as reflected by Yic.

Use of the wellness factor Z to adjust the executed stimulation program is also particularly useful because the stimulation program may be sub-threshold—i.e., at a level that the patient can't directly feel. In this circumstance, it may be difficult for the patient to provide feedback concerning the effect of changes in the stimulation program, and so the combination of qualitative measurements Xi and quantitative measurements Yi provide a means for quantifying such effects that are otherwise difficult to determine.

The stimulation optimization algorithm 222 may not automatically adjust the patient's stimulation program, but may instead first seek confirmation from the patient (or clinician) that it is authorized to make the adjustment. Thus, as shown in FIG. 10A, if the algorithm 222 determines that wellness factor Z is not optimal, the algorithm 222 may send a request to change the stimulation program (CSP) signal to an external device, such as the patient external controller 160. If signal CSP is received at the external controller 160, the user may be prompted that his stimulation program may be adjusted, such as at interface aspect 137 of the Wellness Menu (FIG. 8). Upon receiving this prompt, the user may then choose to allow the algorithm 222 to change the stimulation program (Y/N), which response can be wirelessly communicated to the IPG or ETS. In a more complicated example, the algorithm 222 can additionally transmit to the external device the specific changes in the stimulation program it is recommending, i.e., how the algorithm 222 proposes to change amplitude, pulse width, frequency, etc. Communication of CSP to a relevant external device is not shown in subsequent examples for simplicity, but could be used in such examples as well.

FIG. 10B shows another example in which the wellness modeling algorithm 140 is in the external controller 140, but transmits the determined wellness factor Z to the IPG 110 or ETS 150. Such transmission can occur on a periodic basis or whenever Z is calculated, and whenever the external controller 160 is coupled for communication with the IPG 110 or ETS 150. The stimulation optimization algorithm 222 can then adjust the stimulation program given Z as previously described.

FIG. 10C show another alternative in which the wellness modelling algorithm 140 operates within the clinician programmer 170 to determine wellness factor Z, as occurred in FIG. 9C. In this example, the wellness factor Z can be transmitted to the external controller 160, which in turn can transmit Z to the circuitry 220 in the IPG 110 or ETS 150. Alternatively, the clinician program 170 can directly transmit the determined wellness factor Z to the IPG 110 or ETS 150, for example using its antennas 80a or 80b (FIG. 4). Again, the stimulation optimization algorithm 222 can adjust the stimulation program given Z as previously described.

In FIGS. 10D and 10E, the stimulation optimization algorithm 222 is embodied in the external controller 160 and the clinician programmer 170 respectively. In FIG. 10D, the wellness modelling algorithm 140 in the external controller 160 determines wellness factor Z and provides it to the stimulation optimization algorithm 222 also in the external controller. This allows the external controller 160 to determine, or adjust, the stimulation program that the external controller provides to the IPG 110 or ETS 150 for execution. In FIG. 10E, the wellness modelling algorithm 140 in the clinician programmer 170 determines wellness factor Z and provides it to the stimulation optimization algorithm 222 also in the clinician programmer. Again, this allows the clinician programmer 170 to determine, or adjust, the stimulation program that the clinician programmer provides to the IPG 110 or ETS 150 for execution. Note that the clinician programmer 170 can provide the adjusted stimulation program to the IPG 110 or ETS 150 via the external controller 160, as shown in dotted lines.

The wellness modelling algorithm 140 and the stimulation optimization algorithm 222 need not be embodied in the same device in the system. For example, one algorithm may reside in the clinician programmer while the other resides in the external controller 160. More generally, given the communicative connectivity of the various devices in the system, the algorithms 140 and 222 can be distributed between the clinician programmer 170, the external controller 160 and the IPG 110 or ETS 150 in any fashion. Furthermore, although not shown, algorithms 140 and 222 may also reside in an external sensor 120 (FIG. 5).

To this point, aspects of the invention have been illustrated in the context of SCS therapy as useful to curb pain and DBS therapy as useful to curb tremor and neuropsychiatric disorders. However, useful examples of the invention are not so limited, and instead the invention may be used in other contexts in which a medical device's therapy effectiveness in treating a patient's symptoms is gauged using qualitative and quantitative measures to compute a wellness factor, and in which such wellness factor may be used to adjust the therapy that the medical device provides. In this regard, the invention may be used with medical devices that are not implantable. The invention can be used in a Peripheral Nerve Stimulation (PNS) system (whether implantable or not), a Transcutaneous Electrical Nerve Stimulation (TENS) system, and in other stimulation therapy systems. The invention may further be used in medical device systems that provide therapies other than neurostimulation. The invention may also be used to compare the effectiveness of different types of therapies to address a patient's symptoms, or to evaluate multi-modal therapies.

Wellness modelling algorithm 140 and stimulation optimization algorithm 222 can comprise instructions executed by the control circuitry in the relevant device in the system (e.g., the clinician programmer 170, the external controller 160 or the IPG or ETS), which instructions can be stored in non-transitory computer readable media, such as solid state, magnetic, optical memories, etc. Because the algorithms 140 and 222 may reside at different locations within the system, there may be one or more computer readable media that store them, or they may be stored together in one medium. Such computer readable media may also include instructions to operate the various graphical user interfaces at the external devices. Relevant computer readable media may also include those present in devices connectable to the medical device system, such as Internet or other servers from which the algorithms can be downloaded.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical device system, comprising:
a medical device configured to execute a program to alleviate a symptom of a patient; and
at least one non-transitory computer readable medium containing instructions for a first algorithm, wherein the first algorithm when executed is configured to:
receive at least one qualitative measurement from the patient regarding the symptom, wherein the at least one qualitative measurement comprises subjective input from the patient regarding their perception of how therapy is affecting the symptom,
receive a plurality of quantitative measurements taken from the patient, and
determine a wellness factor for the patient using the at least one qualitative measurement and the plurality of quantitative measurements.

2. The medical device system of claim 1, wherein the first algorithm is configured to be executed on an external device configured to adjust the program executed by the medical device.

3. The medical device system of claim 2, wherein the first algorithm is further configured to receive at least one of the quantitative measurements from at least one sensor of the external device.

4. The medical device system of claim 2, wherein the at least one non-transitory computer readable medium contains further instructions configured when executed to provide a graphical user interface on the external device, wherein the graphical user interface is configured to receive the at least one qualitative measurement and to provide the at least one qualitative measurement to the first algorithm.

5. The medical device system of claim 2, wherein the medical device comprises at least one sensor configured to provide at least one of the quantitative measurements to the first algorithm.

6. The medical device system of claim 1, wherein the system further comprises an external device configured to allow a patient to adjust the program executed by the medical device, wherein the at least one non-transitory computer readable medium is stored in the external device.

7. The medical device system of claim 6, wherein the external device comprises at least one sensor configured to provide at least one of the quantitative measurements to the first algorithm.

8. The medical device system of claim 6, wherein the external device comprises a graphical user interface configured to allow the patient to enter the at least one qualitative measurement and to provide the at least one qualitative measurement to the first algorithm.

9. The medical device system of claim 6, wherein the medical device comprises at least one sensor configured to provide at least one of the quantitative measurements, and to transmit the at least one of the quantitative measurement to the first algorithm in the external device.

10. The medical device system of claim 1, wherein the at least one non-transitory computer readable medium is stored in the medical device.

11. The medical device system of claim 10, wherein the medical device comprises at least one sensor configured to provide at least one of the quantitative measurements to the first algorithm.

12. The medical device system of claim 1, wherein the quantitative measurements are affected by the symptom, and/or wherein the wellness factor is indicative of the severity of the symptom.

13. The medical device system of claim 1, wherein the first algorithm is configured to determine the wellness factor for the patient by correlating the plurality of quantitative measurements to the at least one qualitative measurement.

14. The medical device system of claim 13, wherein the first algorithm is configured to estimate a qualitative measurement for each quantitative measurement.

15. The medical device system of claim 14, wherein the first algorithm is configured to determine a correlation coefficient between each quantitative measurement and each at least one qualitative measurement.

16. The medical device system of claim 15, wherein the first algorithm is configured to determine the wellness factor by weighting the estimated qualitative measurement for at least some of the quantitative measurements using the correlation coefficients for the at least some of the quantitative measurements.

17. The medical device system of claim 14, wherein the wellness factor comprises at least some of the estimated qualitative measurements.

18. The medical device system of claim 1, wherein the medical device comprises an implantable neurostimulator or an external trial stimulator.

19. The medical device system of claim 1, wherein the at least one non-transitory computer readable medium further contains instructions for a second algorithm, wherein the second algorithm when executed is configured to adjust the program executed by the medical device using the wellness factor.

20. The medical device system of claim 19, wherein the medical device comprises an implantable neurostimulator configured to execute a stimulation program, and wherein the second algorithm when executed is configured to adjust an amplitude of the stimulation program.

* * * * *